(12) United States Patent
Mande et al.

(10) Patent No.: US 9,014,987 B2
(45) Date of Patent: Apr. 21, 2015

(54) ANALYSIS OF COMMUNITY STRUCTURES IN ENVIRONMENTAL SAMPLES

(75) Inventors: Sharmila Shekhar Mande, Hyderabad (IN); Kuntal Kumar Bhusan, Hyderabad (IN); Tarini Shankar Ghosh, Hyderabad (IN)

(73) Assignee: Tata Consultancy Services Limited, Mumbai (IN)

( * ) Notice: Subject to any disclaimer, the term of this patent is extended or adjusted under 35 U.S.C. 154(b) by 540 days.

(21) Appl. No.: 13/331,557

(22) Filed: Dec. 20, 2011

(65) Prior Publication Data

US 2013/0158880 A1   Jun. 20, 2013

(30) Foreign Application Priority Data

Oct. 28, 2011 (IN) .......................... 3044/MUM/2011

(51) Int. Cl.
*G06F 19/26* (2011.01)
*G06F 19/14* (2011.01)
*G06T 11/20* (2006.01)
*G06F 19/20* (2011.01)
*G06F 19/28* (2011.01)

(52) U.S. Cl.
CPC ............... *G06F 19/26* (2013.01); *G06F 19/14* (2013.01); *G06T 11/206* (2013.01); *G06F 19/20* (2013.01); *G06F 19/28* (2013.01)

(58) Field of Classification Search
CPC .............................. G06F 19/26; G06T 11/206
See application file for complete search history.

(56) References Cited

U.S. PATENT DOCUMENTS

2006/0246444 A1* 11/2006 van der Vossen et al. ........ 435/6

OTHER PUBLICATIONS

Borg, I. & Groenen, P. J. F. "How to Obtain Proximities". Chapter 6 of Modern Multidimensional Scaling: Theory and Applications. (Springer Science+Business Media, LLC, 2005). pp. 111-133.*
Chaffron, S., Rehrauer, H., Pernthaler, J. & von Mering, C. A global network of coexisting microbes from environmental and whole-genome sequence data. Genome Res. 20, 947-959 (2010).*
Chao, A., Chazdon, R. L., Colwell, R. K. & Shen, T.-J. Abundance-based similarity indices and their estimation when there are unseen species in samples. Biometrics 62, 361-371 (2006).*
Enright, A. J., Van Dongen, S. & Ouzounis, C. A. An efficient algorithm for large-scale detection of protein families. Nucleic Acids Res. 30, 1575-1584 (2002).*
Gansner, E. R. Graphviz Library Drawing Manual. Software documentation. (2007). at <http://www.graphviz.org/doc/libguide/libguide.pdf>.*
Kamada, T. & Kawai, S. An algorithm for drawing general undirected graphs. Inf. Process. Lett. 31, 7-15 (1989).*

(Continued)

*Primary Examiner* — Soren Harward
(74) *Attorney, Agent, or Firm* — Barnes & Thornburg LLP

(57) ABSTRACT

Systems and methods for analyzing community structures within a plurality of environmental samples are described herein. The method includes obtaining taxa data corresponding to taxonomic groups within the plurality of the environmental samples. Based on the taxa data, an abundance value for each of the taxonomic groups with respect to each of the plurality of environmental samples is determined. Further, based on abundance values, an interaction factor for each pair of the taxonomic groups in the plurality of environmental samples is computed. The interaction factor is indicative of a degree of interaction between a pair of taxonomic groups from among the taxonomic groups. Based in part on interaction factors and abundance values, the plurality of the environmental samples is clustered.

19 Claims, 8 Drawing Sheets

(56) References Cited

OTHER PUBLICATIONS

Steele, J. A. et al. Marine bacterial, archaeal and protistan association networks reveal ecological linkages. ISME J. 5, 1414-1425 (2011).*

Sul, W. J. et al. Bacterial community comparisons by taxonomy-supervised analysis independent of sequence alignment and clustering. Proc. Natl. Acad. Sci. USA 108, 14637-14642 (2011).*

Altintas, I. et al. CAMERA 2.0: A Data-centric Metagenomics Community Infrastructure Driven by Scientific Workflows. in 2010 6th World Congress on Services 352-359 (IEEE, 2010).*

Huson, D. H., Richter, D. C., Mitra, S., Auch, A. F. & Schuster, S. C. Methods for comparative metagenomics. BMC Bioinformatics 10 Suppl 1, S12:1-10 (2009).*

Markowitz, V. M. et al. IMG/M: a data management and analysis system for metagenomes. Nucleic Acids Research 36, D534-538 (2008).*

Meyer, F. et al. The metagenomics RAST server—a public resource for the automatic phylogenetic and functional analysis of metagenomes. BMC Bioinformatics 9, 386:1-8 (2008).*

Dethlefsen et al., "The Pervasive Effects of an Antibiotic on the Human Gut Microbiota, as Revealed by Deep 16S rRNA Sequencing," PLoS Biology, Nov. 2008, vol. 6(11), pp. 2383-2400.

* cited by examiner

ANALYSIS OF COMMUNITY STRUCTURES IN ENVIRONMENTAL SAMPLES

CROSS-REFERENCE TO RELATED APPLICATION

This application claims priority under 35 U.S.C. §119 to Indian Application No. 3044/MUM/2011, filed on Oct. 28, 2011, the entirety of which is incorporated herein by reference.

TECHNICAL FIELD

The present subject matter relates, in general, to analysis of environmental samples and, in particular, to analysis of community structures across various environmental metagenomic samples.

BACKGROUND

The study of genetic material recovered directly from an environmental sample by sequencing the genetic material is referred to as metagenomics. Metagenomics provides information pertaining to taxonomic diversity and physiology of various organisms present in an environmental sample. In order to gather information pertaining to taxonomic classification and community structure of an environmental sample, the genetic material obtained directly from the environmental sample is sequenced into a plurality of sequences, called metagenomic sequences.

Taxonomic classification of these metagenomic sequences helps reconstructing the community structure of the environmental sample. Further, to understand microbial ecology of various environmental samples and identify the key organisms responsible for the specific phenotypic characteristic exhibited by an environmental sample, such as specific disease conditions or physiological disorders like obesity, the community structures within the various environmental samples may be compared. Various techniques have been implemented to perform a comparative analysis of the community structures. Generally such techniques seek to group or differentiate the environmental samples based only on the presence or absence of a specific organism(s) under certain environmental conditions. As a result, such techniques may provide an incomplete picture of structure and dynamics of microbial communities within the environmental samples under analysis.

SUMMARY

This summary is provided to introduce concepts related to analysis of community structures across various environmental samples. These concepts are further described below in the detailed description. This summary is not intended to identify essential features of the claimed subject matter nor is it intended for use in determining or limiting the scope of the claimed subject matter.

Method(s) and a system(s) for analyzing community structures within a plurality of environmental samples are described herein. The method includes obtaining taxa data corresponding to taxonomic groups within the plurality of the environmental samples. Based on the taxa data, an abundance value for each of the taxonomic groups with respect to each of the plurality of environmental samples may be determined. Further, based on abundance values, an interaction factor for each pair of the taxonomic groups in the plurality of environmental samples may be computed. The interaction factor is indicative of a degree of interaction between a pair of taxonomic groups from among the taxonomic groups. Furthermore, based in part on interaction factors and abundance values, the plurality of the environmental samples may be clustered.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1A:
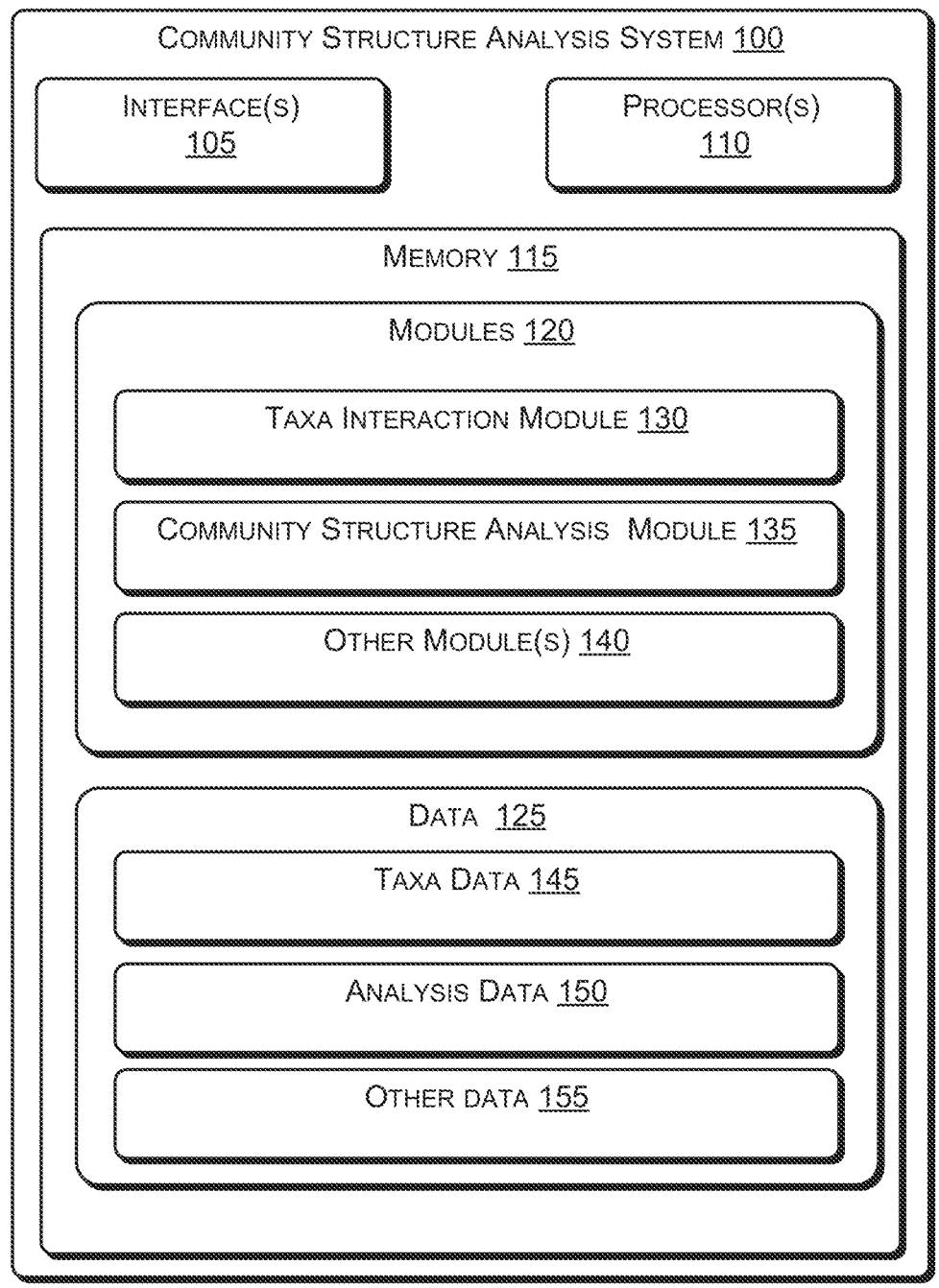
FIG. 1a illustrates various components of a community structure analysis system, in accordance with an embodiment of the present subject matter.

Typically, genetic material extracted directly from an environmental sample, i.e., metagenome, comprises a mixture of nucleic acids originating from different organisms present in that environment. The genetic material is sequenced to generate a plurality of metagenomic sequences, which are subsequently analyzed to understand the community structure of the environmental sample. The community structure may be indicative of the taxonomic diversity of an environmental sample.

The community structures within the environmental samples may be compared to group environmental samples and subsequently identify the key organism(s) conferring specific functional characteristics to a given environmental sample. A specific functional characteristic may not always be attributed to the presence or absence of a specific organism(s) in a given environmental sample, but may be the result of the inter-microbial interactions observed between the resident taxonomic groups. With recent advent of technologies, various techniques are available for performing a comparative analysis of the community structures across various environmental samples. Generally such techniques seek to group or differentiate the environmental samples based on the presence or absence of a specific organism(s) in under certain environmental conditions but may not provide insights into the probable inter-microbial interactions occurring in the given environment. In other words, such techniques may not provide any insights as to how the different groups of organisms are influenced by the other co-inhabiting microbial groups. Further, the comparison provided by such techniques may be difficult to interpret in case of large data sets, i.e., in case community structures are large in size.

According to an embodiment of the present subject matter, methods and systems for analysis of community structures across various environmental samples are described herein. In an implementation, abundance values for each of the taxonomic groups in each of the environmental sample may be determined. The abundance values may indicate how common or rare a taxonomic group is, in a given environmental sample. The abundance value may be determined based on a taxonomic summary file associated with each of the environmental samples. Further, in an example, the abundance values corresponding to each of the taxonomic groups may be normalized with respect to sizes of the environmental samples. The size of the environmental sample may be represented by way of number of assigned sequences, i.e., number of sequences that are assigned to a taxonomic group upon taxonomic classification, or number of assigned operational taxonomic units (OTUs), i.e., number of the OTUs that are obtained upon the taxonomic classification.

Upon determining the abundance values, for each taxonomic group, an interaction factor with respect to each of the remaining taxonomic group may be computed. The interaction factor may be indicative of a degree of interaction between any two taxonomic groups. Further, based on the interaction factors, a taxa interaction profile may be generated. The taxa interaction profile may be indicative of interactions among the various taxonomic groups. For example, the taxonomic groups that show strong positive interactions may be grouped together and the ones that show strong negative interactions with these taxonomic groups may be placed far apart. Such arrangement of the taxonomic groups ensures that the taxonomic groups whose abundance patterns follow a similar trend, i.e., their abundance values increase or decrease similarly across the various environmental samples get placed proximate to each other, while those whose abundance patterns differ are placed distally. In an implementation, the taxa interaction profile is a graphical layout, for instance, the taxonomic groups may be placed on one of the axis of a two dimensional plane.

Further, based on the taxa interaction profile, a community structure analysis profile may be generated. For example, all the environmental samples may also be arranged on the same graphical layout as that of the taxa interaction profile. The community structure analysis profile may be generated based on a force factor corresponding to each of the environmental samples. The force factor for a given environmental sample is computed with respect to its constituent taxonomic groups. The force factor is a function of abundance values of the constituent taxonomic groups and the interaction factors obtained for the constituent taxonomic groups. In one example, the force factor on an environmental sample may be a summation of force vectors due to the individual taxonomic groups on the environmental sample. Owing to such an arrangement of the environmental samples, the environmental samples having similar community structure are placed not only close to each other but also close to the taxonomic groups which are abundant in that environmental sample.

Thus, the present subject matter, in addition to considering relative abundance of the taxonomic groups, also considers biological relevance of each taxonomic group in a community structure. Further, the present subject matter not only provides information pertaining to interaction patterns of taxonomic groups within various community structures but also helps differentiate the community structures of the underlying environmental samples, based on the interactions among the various taxonomic groups. The present subject matter has applicability in various fields of metagenomics research, such as healthcare, environmental microbiology, bioremediation, and industrial biotechnology.

While aspects of described systems and methods for analysis of community structures across various environmental samples can be implemented in any number of different computing systems, environments, and/or configurations, the embodiments are described in the context of the following exemplary system(s).

FIG. 1a illustrates various components of a community structure analysis (CSA) system 100, according to an embodiment of the present subject matter. The CSA system 100, hereinafter referred to as the system 100, can be implemented in computing systems that include, but are not limited to, desktop computers, hand-held devices, multiprocessor systems, personal digital assistants (PDAs), laptops, network computers, cloud servers, minicomputers, mainframe computers, and the like. In one implementation, the system 100 includes interface(s) 105, one or more processor(s) 110, and a memory 115 coupled to the processor(s) 110.

The interfaces 105 may include a variety of software and hardware interfaces, for example, interfaces for peripheral device(s), such as a keyboard, a mouse, an external memory, and a printer. Further, the interfaces 105 may enable the system 100 to communicate with other computing systems, such as web servers and external databases. The interfaces 105 can facilitate multiple communications within a wide variety of networks and protocol types, including wired networks, for example, local area network (LAN), cable, etc., and wireless networks such as Wireless LAN (WLAN), cellular, or satellite. For the purpose, the interfaces 105 may include one or more ports for connecting a number of computing systems with one another or to another server computer.

The processor 110 can be a single processing unit or a number of units, all of which could include multiple computing units. The processor 110 may be implemented as one or more microprocessors, microcomputers, microcontrollers, digital signal processors, central processing units, state machines, logic circuitries, and/or any devices that manipulate signals based on operational instructions. Among other capabilities, the processor 110 is configured to fetch and execute computer-readable instructions and data stored in the memory 115.

The memory 115 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 115 also includes modules 120 and data 125.

The modules 120, amongst other things, include routines, programs, objects, components, data structures, etc., which perform particular tasks or implement particular abstract data types. The modules 120 further include a taxa interaction module 130, a community structure (CS) analysis module 135, and other module(s) 140. The other modules 140 may include programs that supplement applications on the system 100, for example, programs in the operating system. On the other hand, the data 125 serves, amongst other things, as a repository for storing data processed, received, and generated by one or more of the modules 120. The data 125 includes taxa data 145, analysis data 150, and other data 155. The other data 155 includes data generated as a result of the execution of one or more modules in the other modules 140.

In one implementation, the system 100 receives taxonomic summary files corresponding to environmental samples under study. The taxonomic summary file may indicate how abundant a taxonomic group, or taxon, is in a given environmental sample. Thus, the taxonomic summary file of an environmental sample may include a list of constituent taxonomic groups or taxa along with their abundance values. Further, the taxonomic summary files may include a list of organisms at various levels of the taxonomic groups, such as super kingdom, Phylum, Class, Order, Family, Genus and Species. The taxonomic summary files may be in a format, for example, 'bin_stats' format, the standard 'OTU' table, the visualization and analysis of microbial population structures (VAMPS) summary output and simple tab delimited taxonomic summary files.

The taxonomic summary files corresponding to each of the environmental sample may be stored in the taxa data 145. The taxonomic summary files may be received from an external taxonomic classification system or may be determined by the system 100 itself. For example, the other modules 140 may implement any taxonomic classification technique to create a taxonomic summary file for each of the environmental samples. Further, the other modules 140 may also include parsers to convert taxonomic summaries available in other formats, such as 'rma' format and the standard 'rdp' format to the 'bin_stats' format.

In order to analyze the community structures within the various environmental samples, the taxa interaction module 130, for a given taxonomic level, may determine taxonomic groups present in each of the environmental samples. The taxonomic level may be selected by a user or may be set to a default taxonomic level. Further, using the taxonomic summary files, the taxa interaction module 130 may determine abundance values of each taxonomic group in each of the environmental samples. In an example, the abundance values may be in terms of number of assigned sequences or assigned OTUs.

In one implementation, the taxa interaction module 130 may normalize the abundance values based on the size of each of the environmental samples under study. Similar to abundance values, the size of an environmental sample may also be expressed terms of number of assigned sequences or assigned OTUs. The size of each of the environmental sample may be obtained from the taxa data 145. For example, an environment sample $S_1$ may include 1000 assigned sequences and out of these 1000 sequences, 100 sequences may correspond to taxonomic group $T_1$, then the abundance value for $T_1$ in $S_1$ after normalization would be 0.1. Similarly, abundance value for $T_1$ in another sample $S_2$, having 500 assigned sequences, after normalization may be 0.2. Further, the taxa interaction module 130 may also determine average abundance values of each of the taxonomic groups across all the environmental samples under study. The abundance values and average abundance values may be stored in the analysis data 150.

Thus, the taxa interaction module 130 may determine abundance values of each of the taxonomic groups. Upon determining the abundance values, the taxa interaction 130 module may compute an interaction factor for each of the taxonomic groups with respect to each one of the remaining taxonomic group. The interaction factor is indicative of degree of interaction between any two taxonomic groups. In an example, the interaction factor may be computed using following formula:

$$r_{xy} = \frac{\sum_{i=1}^{n}(x_i - x_A)(y_i - y_A)}{\sqrt{\sum_{i=1}^{n}(x_i - x_A)^2 \sum_{i=1}^{n}(y_i - y_A)^2}} \quad (1)$$

where, $r_{xy}$ is correlation coefficient for taxonomic groups x and y, n is the total number of environmental samples under study, $x_i$ and $y_i$ are abundance values of taxonomic groups x and y in the $i^{th}$ environmental sample, where i=1, 2 . . . n; and $x_A$ and $y_A$ are the means of the abundance values of taxonomic groups x and y across n environmental samples. The correlation coefficient, $r_{xy}$, may have a value in the range of +1 to −1. The value of the correlation coefficient, $r_{xy}$, closer to +1 indicate strong or positive interaction between the taxonomic groups x and y, while negative value of the correlation coefficient, $r_{xy}$, indicate negative or inhibitory interaction. Also, correlation coefficient, $r_{xy}$, having value '0' may indicate no correlation.

Further, using the correlation coefficient, the interaction factor may be determined in terms of correlation distances. In an example, the interaction factor may be determined using following expression:

$$I_{xy} = 1 - r_{xy} \quad (2)$$

where $I_{xy}$ is interaction factor indicating interaction between taxonomic groups x and y and $r_{xy}$ is correlation coefficient for taxonomic groups x and y. The interaction factors provide quantitative measures of the relationship between taxonomic groups and may not be dependent on the absolute sizes of the environmental samples being analyzed. The closer the value of the interaction factor is to 0, the stronger is the positive interaction between the taxonomic groups x and y. Thus, the interaction factor having value close to 0 indicates a symbiotic relationship between taxonomic groups x and y and the interaction factor having value close to 2 indicates an inhibitory relation between the taxonomic groups x and y. Also the interaction factors having value closer to 1 may indicate no correlation between the taxonomic groups x and y. The interaction factors and the correlation coefficients may be stored in the analysis data 150.

In one implementation, upon computing the interaction factors for each pair of the taxonomic groups, the CS analysis module 135 may generate a taxa interaction profile based on interaction factors of the taxonomic groups. The CS analysis module 135 may implement a classical hierarchical clustering methodology to generate the taxa interaction profile. In an example, to generate the taxa interaction profile, the CS analysis module 135 may randomly start with a taxonomic group, say, $T_1$. Based on a value of an interaction factor associated with $T_1$ with respect to each of the rest of the taxonomic groups, say, $T_2, T_3 \ldots T_N$, the rest of the taxonomic groups are assigned a rank. For example, the interaction factor, $I_{T1, T3}$, indicating interaction between $T_1$ and $T_3$, may have the lowest value so it may be given the highest rank, while interaction factor, $I_{T1, T2}$, indicating interaction between $T_1$ and $T_2$ may have the highest value so it may be given the lowest rank. Further, the taxonomic groups may be arranged based on their ranks Thus, the taxonomic groups, i.e., the taxonomic groups from $T_2$ to $T_N$, which have strong interaction with the taxonomic group $T_1$ are placed near the taxonomic group $T_1$ based on the classical hierarchical clustering methodology. Similarly the taxonomic groups having inhibitory relation with the taxonomic group $T_1$ are placed away from the taxonomic group $T_1$. In one implementation, inorder to refine the arrangement, the above process can be repeated for other taxonomic groups, such as one or more taxonomic groups from $T_2$ to $T_N$.

In an example, the taxa interaction profile is in the form of a graphical layout. In the said example, the taxonomic groups are first assigned a rank according to their interaction factors. Further, based on the rank, the taxonomic groups are placed on a graphical layout, for example, on one of the axis of a two dimensional layout. Referring to the example mentioned above, the taxonomic group $T_1$ may be placed on x-axis, say, at coordinates {0,0}, and the taxonomic groups having positive correlation with the taxonomic group $T_1$ may be placed near '0' on x-axis, while negatively correlated ones may be placed at a suitable distance on the x-axis.

Such arranging of the different taxonomic groups not only facilitates identification of positively correlated or strongly positively interacting clusters of taxonomic groups but also helps in efficiently resolving or partitioning the different environmental samples based on the similarities in their community structures.

Based on taxa interaction profile, the CS analysis module 135 may cluster the environmental samples to generate a community structure analysis profile. The taxa interaction profile and the community structure analysis profile may be stored in the analysis data 150. The community structure analysis profile, in an example, may also be in the form of a graphical layout. However, it will be understood that the community structure analysis profile may be in any other format as well, for example, tabular format. In an implementation, the community structure analysis profile is generated such that the environmental samples that have similar community structure are placed close to each other. Additionally, each environmental sample is placed close to the taxonomic groups that have high abundance value with respect to that environmental sample.

In an example, to generate the community structure analysis profile, the CS analysis module 135 may determine a center of taxonomic arrangement using the following equation:

$$R = \frac{\sum_{i=1}^{n} m_i(x) r_x}{\sum_{i=1}^{n} m_i(x)} \quad (3)$$

where R is the center of taxonomic arrangement, $r_x$ is the position of a taxonomic group 'x', which may be obtained from the taxa interaction profile, m(x) is calculated as the summation of the normalized abundance values of the taxonomic group 'x' for all the 'n' environmental samples being analyzed.

Upon determining the center of taxonomic arrangement, each of the environmental samples may be placed on a graphical layout, in which the taxa interaction profile was generated. Each of the environmental samples may be placed at an initial height "h" from the point corresponding to the R. Thus, in the two dimensional layout, the environmental samples have initial position as (R, h). The initial height "h" may be calculated dynamically based on one or more dimension parameters. The dimension parameters include, for example, total number of taxonomic groups, size of an axis on which the taxonomic groups are placed, size of a display screen on which the community structure analysis profile will be displayed.

Using the initial position, a final position for each of the environmental samples is determined. The final position of each of the environmental sample may be determined based on a force factor. In an example, the force factor may be determined by computing force vectors on the environmental sample due to each of the taxonomic groups. It may be assumed that from the initial position of an environmental sample, $S_1$, virtual springs are attached to each of the taxonomic groups. The spring constant of each such spring may be a function of an abundance value of the taxonomic group in the environmental sample $S_1$. The force vector representing force exerted on an environmental sample due to the $i^{th}$ taxonomic group may be computed using following equation:

$$F_i = A_i \vec{d}_i \quad (4)$$

where $F_i$ is force vector on the environmental sample, say, $S_1$ due to $i^{th}$ taxonomic group, $A_i$ is the abundance value of the $i^{th}$ taxonomic group in the environmental sample $S_1$, $d_i$ is the displacement of the initial position from the position of the taxonomic group on the x-axis.

Subsequently, the cumulative force on an environmental sample is calculated as the summation of the force vectors due to the individual taxonomic groups. The cumulative force represents the force factor for the environmental sample $S_1$. The force factor is representative of the combined interaction pattern of all the constituent taxonomic groups on the environmental sample $S_1$. The environmental sample $S_1$ is then assigned a final position on the graphical layout based on the resultant displacement. The same process may be repeated for all the environmental samples being analyzed. The graphical layout then displays the positions of the various taxonomic groups and all environmental samples, thereby providing the community structure analysis profile. Further, the CS analysis module 135 may apply certain transformations on the final layout for better visualization and to improve aesthetics of community structure analysis profile. The CS analysis module 135 may enable the users to compare the studied environmental samples using standard visualization features, such as bar-charts, trend-graphs, and heat-tables.

As it can be observed that the force factor for each environmental sample is a function of the relative abundances of the various taxonomic groups in that environmental sample and also the relative position of each taxonomic group from the environmental sample's initial position. This ensures that the environmental samples are placed in community structure analysis profile in such a manner that environmental samples having similarities in their community structure are not only placed closer to each other but also closer to the taxonomic groups which are abundant in them. Further, the community structures of the various environmental samples are also represented by the community structure analysis profile such that significantly positively correlated taxonomic groups are placed together and negatively correlated ones are placed far apart.

The generation of community structure analysis profile may be understood with the following example. Consider three environmental samples, $S_1$, $S_2$, and $S_3$ and there are total 3 taxonomic groups $T_1$, $T_2$, and $T_3$. Further, from the taxa data 145 it may be determined that $T_1$ is abundant in $S_1$, $S_2$, and $S_3$; $T_2$ is scarcely available in $S_1$ and $S_2$ but absent in $S_3$; and $T_3$ is only available in $S_3$. Also, interaction factor for $T_1$ and $T_2$ may indicate that they are highly interactive. Accordingly, in the community structure analysis profile, the environmental samples $S_1$ and $S_2$ may be placed proximate to each other and near $T_1$ and $T_2$. Although, $S_3$ includes $T_1$ in abundance it may not be placed proximate to $S_1$ and $S_2$, since it does not have the same interaction pattern for $T_1$ and $T_2$ as indicated by the other two environmental samples $S_1$ and $S_2$. Thus, the present subject not only considers abundance a taxonomic group across various environmental samples but also its interaction with other taxonomic groups, which may be available in scarce amount in the environmental sample.

The community structure analysis profile may provide information pertaining to similarity of the environmental samples and reasons for specific phenotype of an organism. Further, the community structure analysis profile may indicate relative abundance of each taxonomic group in a community structure, which may be used to assess the contribution of each taxonomic group or a selected set of taxonomic groups that are responsible for the inherent differences across various communities. Furthermore, community structure analysis profile may facilitate identification of taxonomic groups, which are common across all the environmental samples as well as a subset of these taxonomic groups, which are present in specific groups of the environmental samples. The subset of these taxonomic groups may correspond to rare taxonomic groups, which may not be available in abundance in the environmental samples. While the taxonomic groups identified as common to all environmental samples may play a major role in maintaining the equilibrium of the analyzed community structures, the selectively occurring taxonomic groups may be responsible for conferring specific phenotype to the environmental samples.

Additionally, the community structure analysis profile may enable analysis of the inherent interaction network of the taxonomic groups present in a selected set of environmental samples. Further, the community structure analysis profile may be helpful in studies involving environmental samples that are collected from similar but phenotypically distinct habitats, for example, gut environments of lean and obese individuals, or the environmental samples collected from similar habitats, at different points of time, i.e., time series metagenomic data. In such cases, the taxonomic groups constituting the studied community structures are more or less similar, but exhibit subtle differences in their relative proportions. By capturing the correlations in the abundance patterns of the constituent taxonomic groups across such community structures, the community structure analysis profile can provide insights into the inherent interaction dynamics in the given habitat. For example, taxonomic groups showing a positive correlation in their abundance profiles and consequently placed closer to each other in the community structure analysis profile may have a positive symbiotic relationship between them. Similarly, those taxonomic groups that are placed farther apart in the graphical layout may have a negative or inhibitory effect on each other.

Figure 1B:
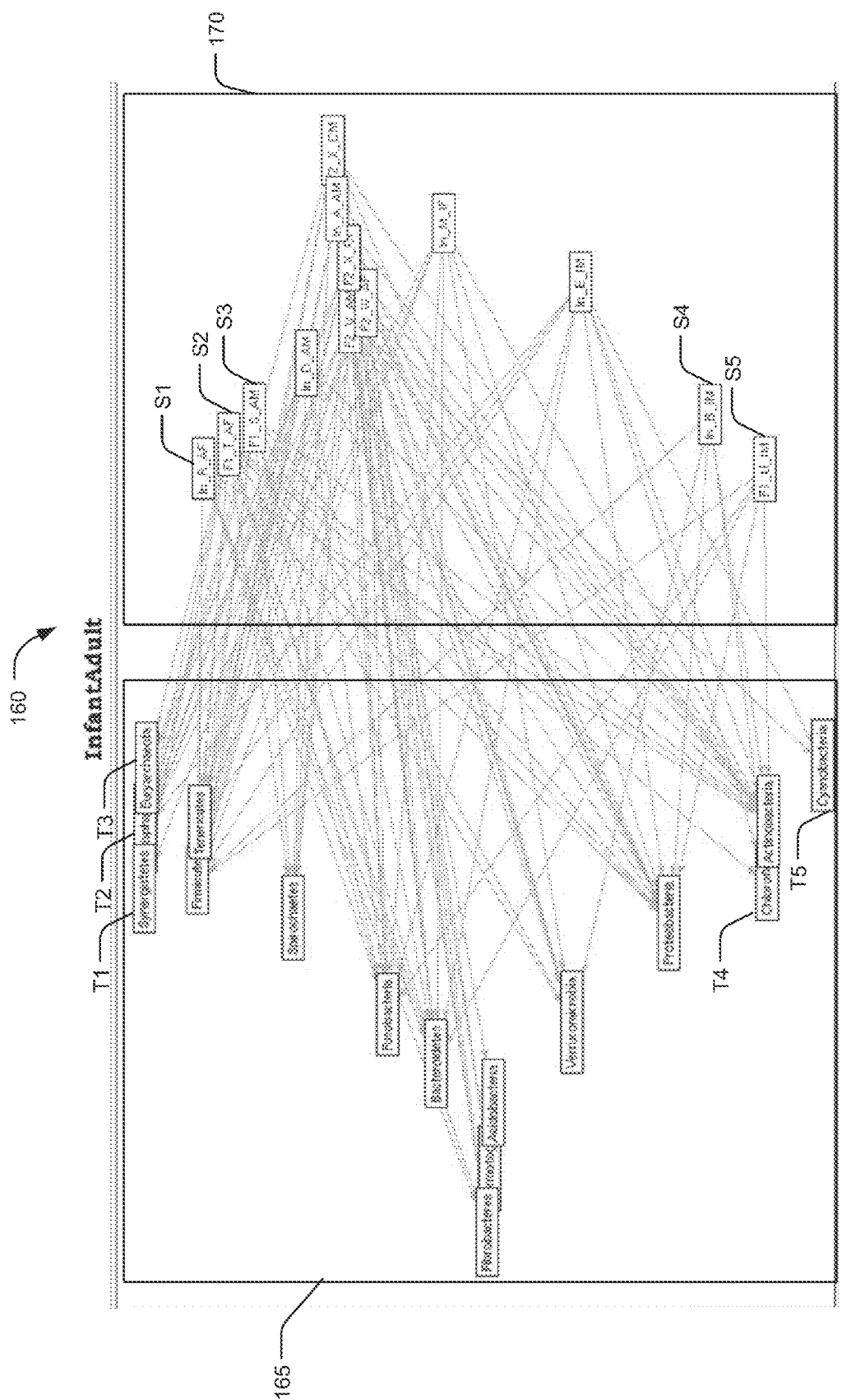
FIG. 1b illustrates a screenshot of a community structure analysis profile, according to an embodiment of the present subject matter.

FIG. 1b illustrates a screenshot of a community structure analysis profile 160, according to an embodiment of the present subject matter. In the community structure analysis profile 160 all the taxonomic groups are indicated in a block 165 and the environmental samples are represented in a block 170. The block 165 illustrates interactions among all the taxonomic groups. As it can be observed from community structure analysis profile 160, the taxonomic groups $T_1$, $T_2$, and $T_3$ that illustrate strong interaction are placed close to each other, while taxonomic groups $T_4$ and $T_5$, which have an inhibitory relation with the taxonomic groups $T_1$, $T_2$, and $T_3$ are placed far apart from them. Further, it can be observed that the environmental samples $S_1$, $S_2$, and $S_3$, are abundant in the taxonomic groups $T_1$, $T_2$, and $T_3$ and the interaction pattern exhibited by these three groups is same in the three samples $S_1$, $S_2$, and $S_3$, therefore these samples are placed close together and also close to the taxonomic groups taxonomic groups $T_1$, $T_2$, and $T_3$. Also, the environmental samples, $S_4$ and $S_5$ having different community structures are placed far apart from the environmental samples $S_1$, $S_2$, and $S_3$. It will be understood that the screenshot is provided only for the purpose of illustration and not as a limitation.

Validation and Results

The results of present CSA system have been validated using a previously reported study on the pervasive effects of treatment using the antibiotic Ciprofloxacin on the gut microbiota of individuals (Dethlefsen et al., 2008). The dataset for community structure analysis constituted 16S rDNA samples collected from the gut of three individuals at various time points, viz., before, during and after the antibiotic treatment. The first individual was a 22 years old Asian female, the second individual was a 36 years old European-American male, and the third individual was a 43 years old European-American male. The samples obtained from three individuals may be referred to as sample A, B, and C. The various stages or time points at which the 16S rDNA samples were collected from the three individuals are depicted in table 1:

TABLE 1

| Interval | Prior Treatment | | | | Post treatment | | | |
|---|---|---|---|---|---|---|---|---|
| | 60 days | 6 days | 2 days | 1 day | 3 days | 5 days | 33 days | 180 days |
| First Individual (Sample A) | A1 | A2a | A2b | A2c | A3a | A3b | A4 | A5 |
| Second Individual (Sample B) | B1 | | B2 | | | B3 | B4 | B5 |
| Third Individual (Sample C) | C1 | | C2 | | | C3 | C4 | C5 |

Figures 1, 2A:
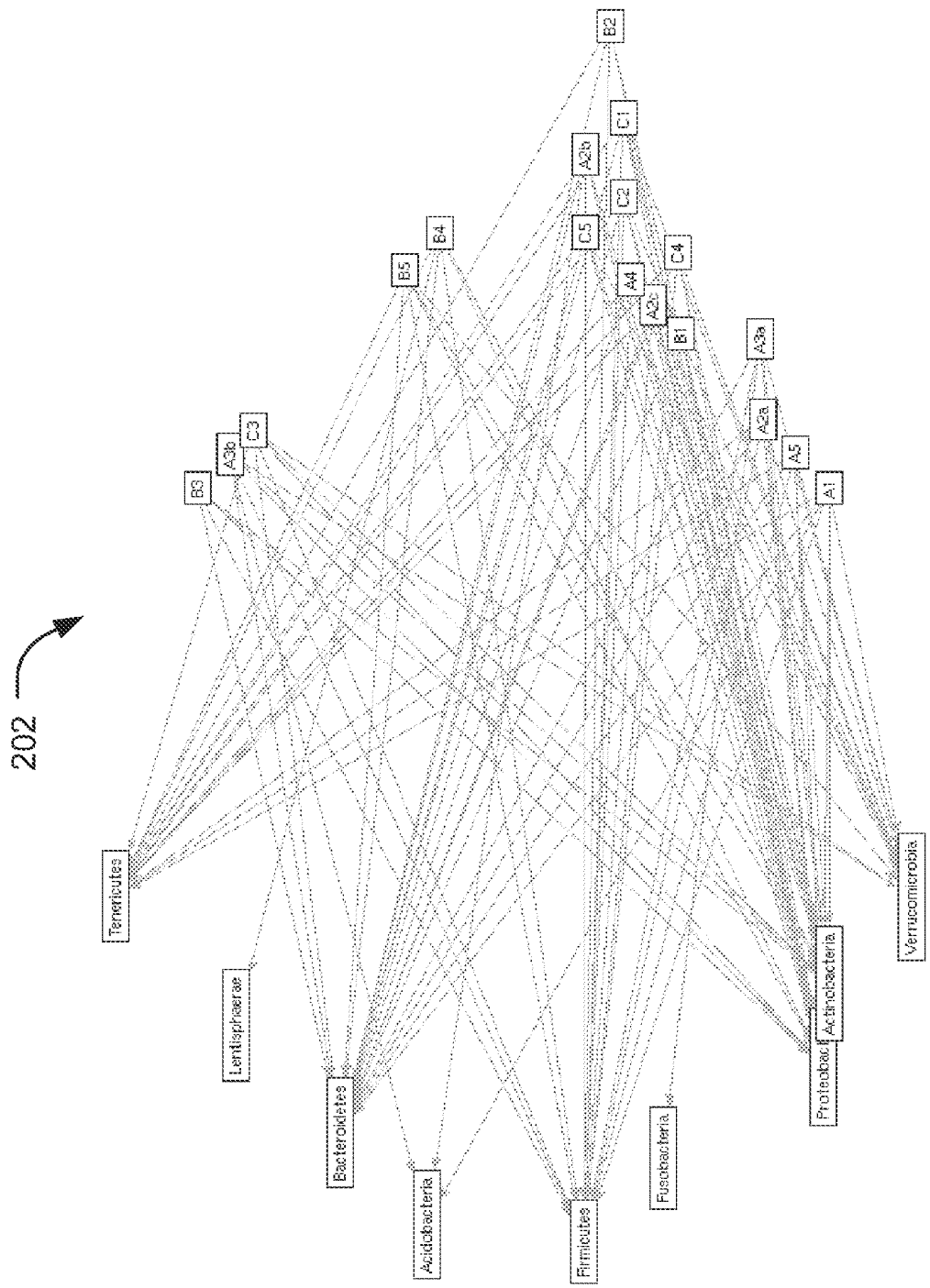
FIGS. 2a, 2b, and 2c illustrate various screenshots indicating experimental results for the present subject matter, according to an embodiment of the present subject matter.
Figures 2, 2A:
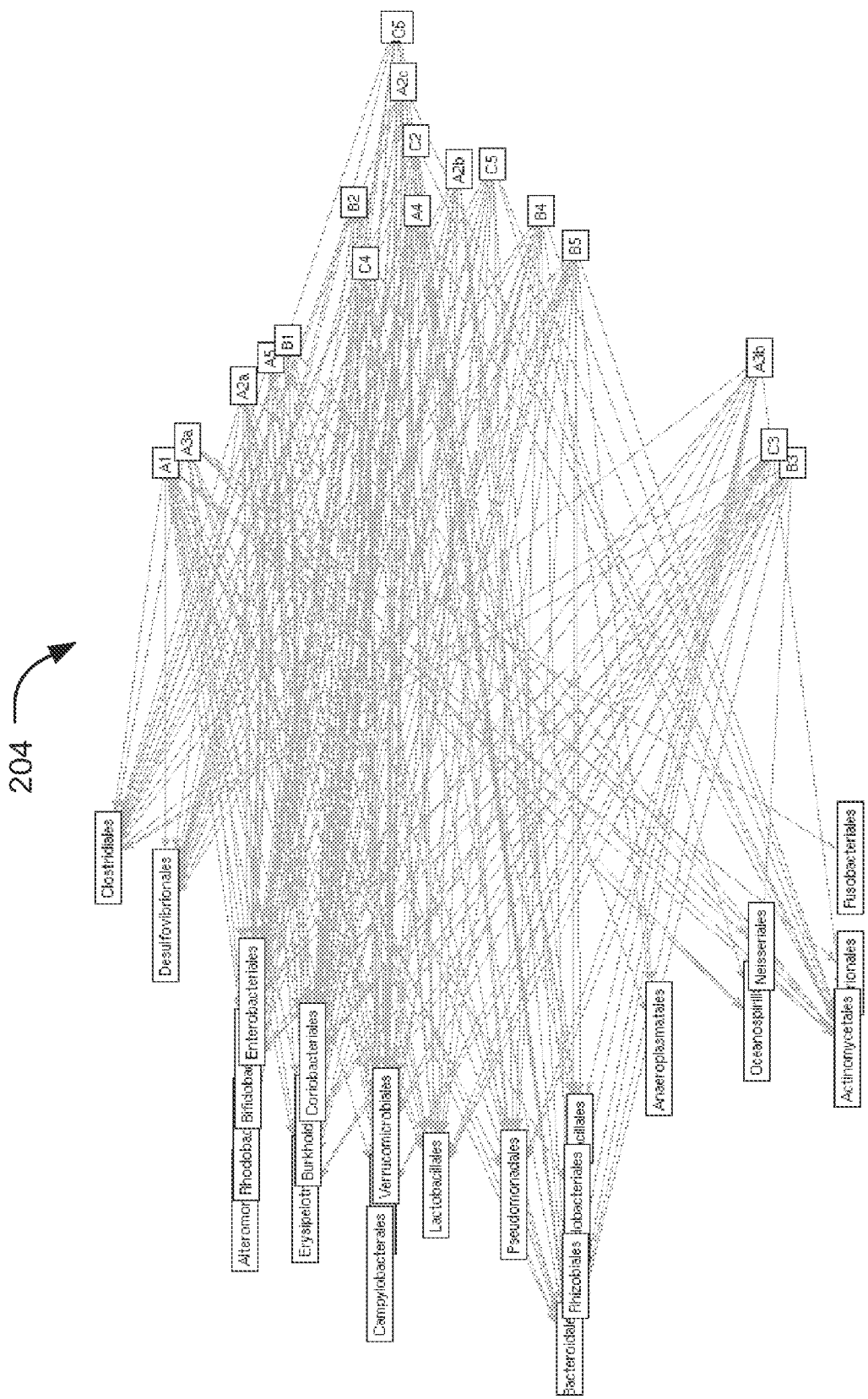

To analyze the community structures, firstly taxonomic summary files corresponding to the three individuals were obtained. Based on the taxonomic summary files using the system 100 the community structure analysis profiles at various taxonomic levels were generated. For the purpose of explanation, the community structure analysis profiles generated at phylum and order level are depicted in FIG. 2a. The community structure analysis profile 202 is generated at the phylum level and the community structure analysis profile 204 is generated at the order level. These community structure analysis profiles helped in understanding the effects of the antibiotic treatment on the gut microbial community of the three individuals. From the analysis of the community structure analysis profile it was determined that for all the three individuals, the samples obtained during antibiotic treatments clustered distinctly from those corresponding to the pre- and post-treatments. Thus, the community structure analysis profiles indicated that the structure of the microbial communities during antibiotic treatment were different from the microbial communities present in pre-treatment and post treatment.

Figures 1, 2B:
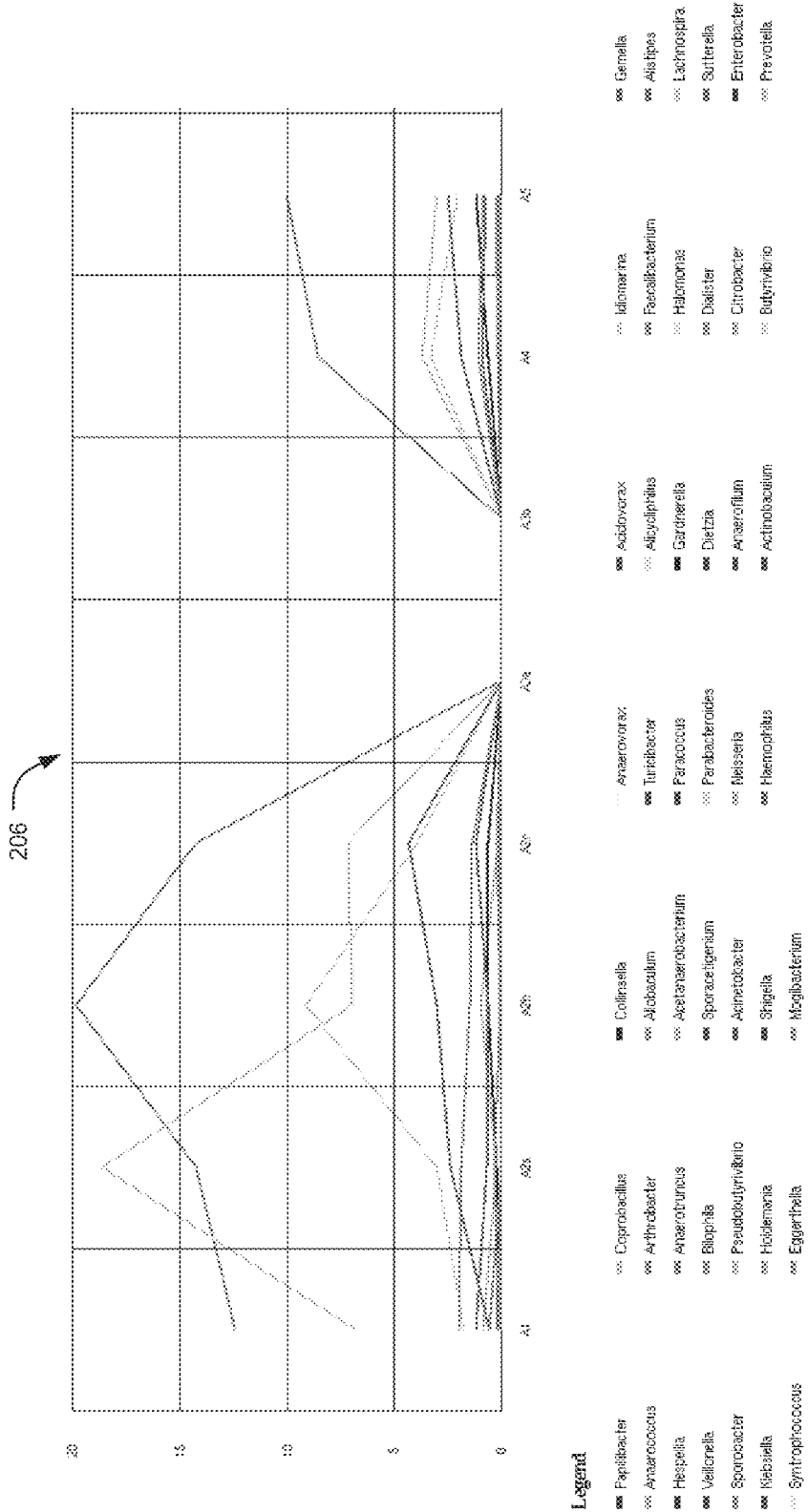
Figures 2, 2B:
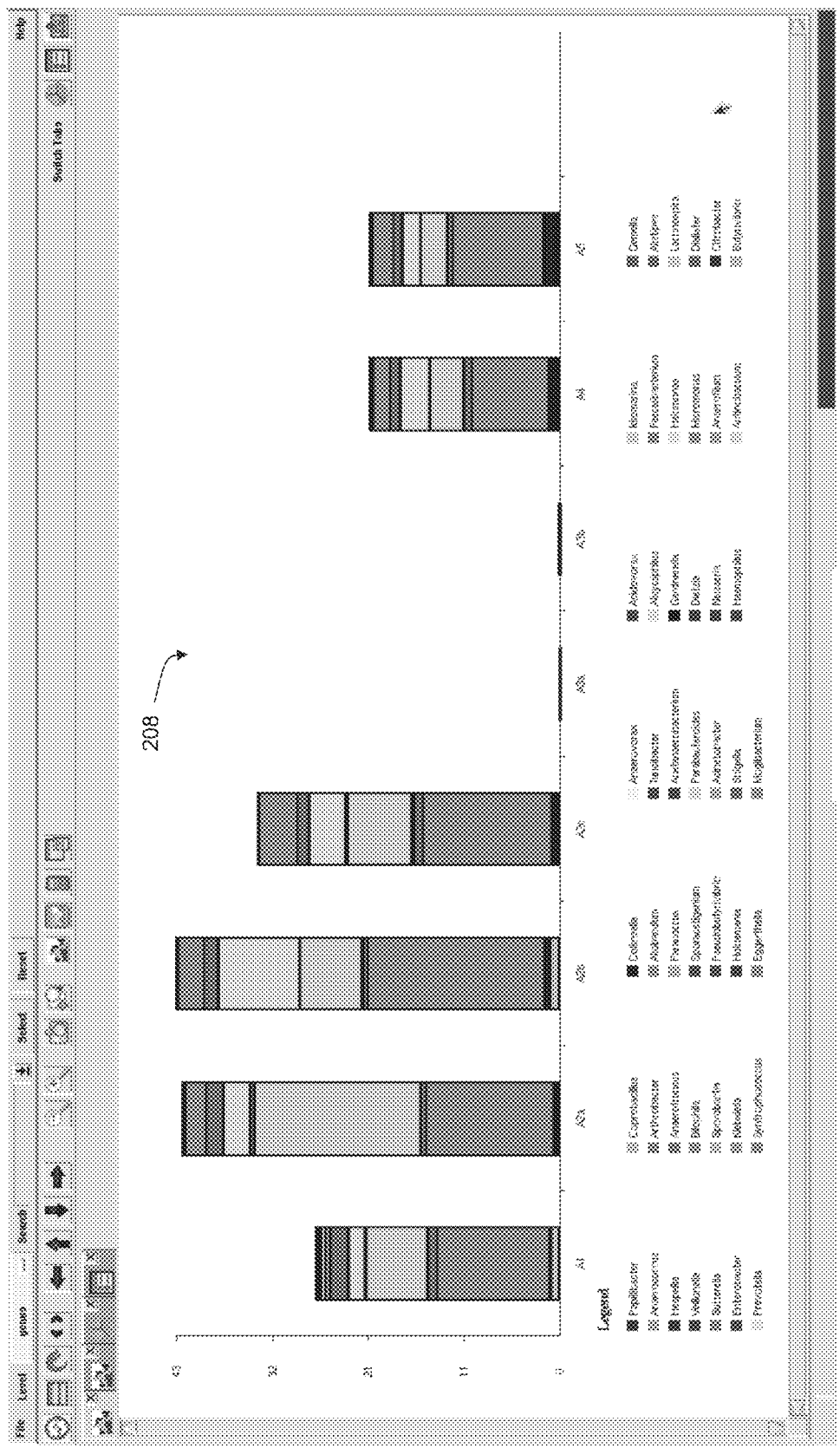

Further, to identify a probable reason for distinct community structure for the microbial communities during antibiotic treatment, the variation of the relative abundances of the different genera at different stages of antibiotic treatment for the sample A, i.e., the first individual using the 'trend plot' and the 'cumulative bar plot' features was studied. A trend plot 206 and a cumulative bar plot 208 are illustrated in FIG. 2b. As it can be observed from the trend plot 206 and the cumulative bar plot 208 that the samples, A3a and A3b, which are the samples that were obtained during the antibiotic treatment, do not include several genera, thereby indicating a drastic decrease in the taxonomic diversity of the underlying gut microbial community.

Figure 2C:
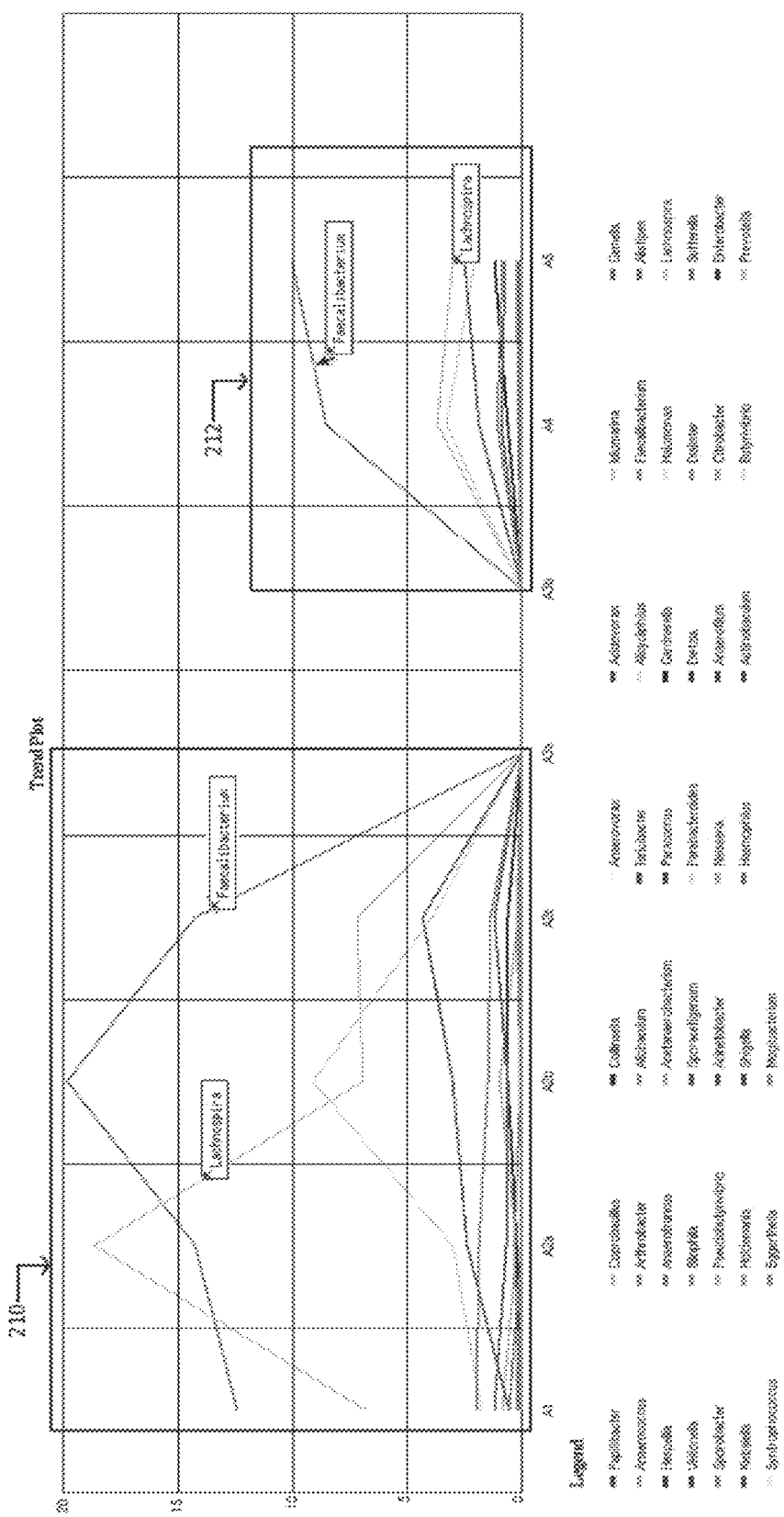

The community structure analysis profiles also indicated that the microbial community structure for the pre-antibiotic and post-antibiotic treated samples had a closer resemblance as compared to those obtained during antibiotic treatment. To study the microbial community structures for the pre-antibiotic and post-antibiotic treated samples, trend plots using the community structure analysis profile were generated. FIG. 2c illustrates trend plots 210 and 212 for pre-antibiotic and post-antibiotic treated samples respectively. It can be observed from the trend plots 210 and 212 that the relative proportions of the different genera in the two samples have noticeably decreased. For example, *Lachnospira* and *Faecalibacterium* showed a noticeably reduced abundance in the post-antibiotic treated samples as compared to the pre-treated samples, indicating that the deleterious effects of antibiotic treatment on these genera are especially pervasive.

Further, the results obtained using the community structure analysis profile were found to be in exact confirmation with those obtained in the original study (Dethlefsen et al., 2008).

Thus, it can be seen that the community structure analysis profile helped in capturing the distinct changes in the gut microbial community during the antibiotic treatment. Additionally, the deleterious effect on the abundances of several microbial groups, leading to a decrease in the taxonomic diversity of the gut microbial community could also be captured easily using community structure analysis profile.

Figure 3:
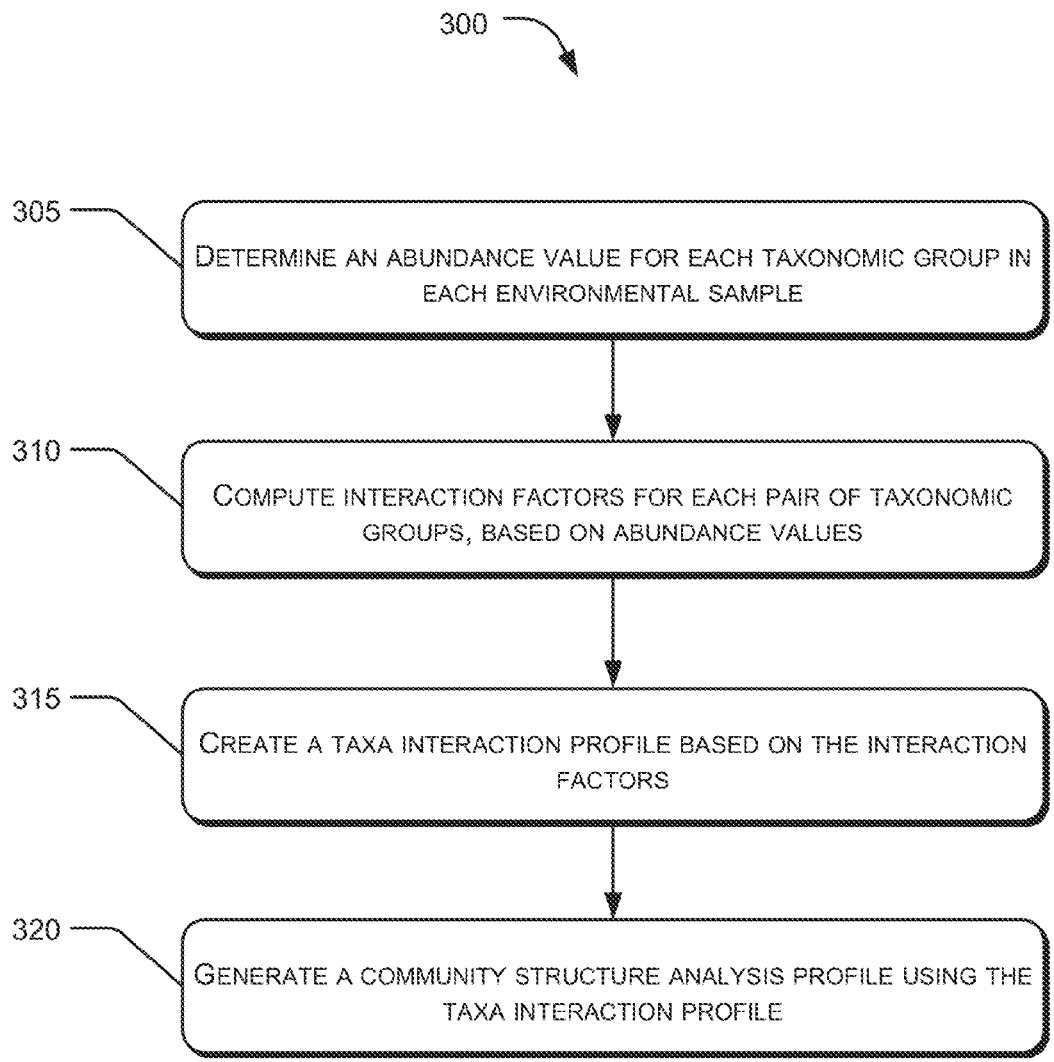
FIG. 3 illustrates a method for generation of community structure analysis profile, in accordance with an implementation of the present subject matter.

FIG. 3 illustrates a method 300 for generating community structure analysis profile, in accordance with an implementation of the present subject matter.

The method may be described in the general context of computer executable instructions. Generally, computer executable instructions can include routines, programs, objects, components, data structures, procedures, modules, functions, etc., that perform particular functions or implement particular abstract data types. The method may also be practiced in a distributed computing environment where functions are performed by remote processing devices that are linked through a communications network.

The order in which the method is described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the method can be implemented in any suitable hardware, software, firmware, or combination thereof.

At block 305, an abundance value for each taxonomic group, in each of a set of environmental samples, may be determined. In one implementation, abundance values may be determined based on a corresponding taxonomic summary file of the environmental sample. Further, in an example, the abundance values may include normalized values based on size of the environmental sample. In an implementation, the taxa interaction module 130 may determine the abundance values.

At block 310, for each pair of taxonomic groups, an interaction factor is computed. In other words, for each taxonomic group an interaction factor with respect to each of the remaining taxonomic group is computed. The interaction factor between two taxonomic groups is computed based on the corresponding abundance values of the two taxonomic groups. In an example, the taxa interaction module 130 may compute the interaction factors.

At block 315, a taxa interaction profile is created based on the interaction factors. The taxa interaction profile is indicative of the interaction among the various taxonomic groups. In an example, the taxa interaction profile is a graphical layout, such as a two dimensional layout. The taxa interaction profile may be created by implementing a hierarchical clustering methodology. In one implementation, the CS analysis module 135 creates the taxa interaction profile.

At block 320, a community structure analysis profile is generated based on the taxa interaction profile. The community structure analysis profile may be generated based on force factors corresponding to each of the environmental sample. Further, the environmental samples may be clustered based in part on the interaction factors and the abundance values to generate community structure analysis profile. In an example, the community structure analysis profile has the same graphical layout as that of the taxa interaction profile. In said example, the environmental samples are placed on the graphical layout based on their corresponding force factors. In one implementation, the CSA module 135 generates the community structure analysis profile.

The community structure analysis profile may allow one to visualize common as well as unique interaction pairs across the selected environmental samples. The identification of such core hubs of interacting taxonomic groups might play a critical role in determining the phenotypical characteristics of the environmental samples under study.

Although embodiments for analysis of community structures within various environmental samples have been described in language specific to structural features and/or methods, it is to be understood that the invention is not necessarily limited to the specific features or methods described. Rather, the specific features and methods are disclosed as exemplary embodiments for analysis of the community structures.

The invention claimed is:

1. A computer implemented method for analyzing community structures within a plurality of environmental samples, the method comprising:

creating a plurality of metagenomic sequences by sequencing genetic material obtained from each of the plurality of environmental samples, wherein the plurality of the metagenomic sequences are analyzed to identify a corresponding taxonomic group;

obtaining, by a processor, a taxonomic summary file corresponding to each of the plurality of the environmental samples, the taxonomic summary file being indicative of an abundance value of the taxonomic group within a corresponding environmental sample;

determining, by the processor, the abundance value for each of the taxonomic groups with respect to each of the plurality of environmental samples, based on obtained taxonomic summary files;

computing, by the processor, an interaction factor for each pair of the taxonomic groups in the plurality of environmental samples, based on corresponding abundance values, to generate a taxa interaction profile, wherein the interaction factor is indicative of a degree of interaction between a pair of taxonomic groups from among the taxonomic groups, and wherein the taxa interaction profile is indicative of interactions among the taxonomic groups;

computing, by the processor, a force vector acting on each of the plurality of the environmental samples due to each of the taxonomic groups, based on the abundance value of each of the taxonomic groups, wherein the force vector is indicative of virtual force exerted by each of the taxonomic groups on the environmental sample;

determining, by the processor, a force factor corresponding to each of the plurality of environmental sample, based on the force vectors corresponding to the environmental sample, the force factor being representative of a combined interaction pattern of the constituent taxonomic groups on the corresponding environmental sample; and clustering, by the processor, the plurality of the environmental samples based on corresponding force factors to generate a community structure analysis profile, wherein the community structure analysis profile includes each of the plurality of environmental samples and each of the plurality of taxonomic groups as a node, and wherein an edge is assigned between an environmental sample and a taxonomic group, and wherein, in the community structure analysis profile, the clustering places each of the plurality of environmental samples in the vicinity of one or more environmental samples having a similar community structure and in the vicinity of one or more taxonomic groups that are abundant in the environmental sample.

2. The computer implemented method as claimed in claim 1, wherein determining the abundance value further comprises normalizing the abundance value for each of the taxonomic groups based on a size of a corresponding environmental sample.

3. The computer implemented method as claimed in claim 2, wherein the size of the corresponding environmental sample denotes one of a total number of assigned sequences in the corresponding environmental sample, and a total number of operational taxonomic units (OTUs) obtained for the corresponding environmental sample.

4. The computer implemented method as claimed in claim 1, wherein computing the interaction factor for each pair of the taxonomic groups comprises:
determining a correlation coefficient between the pair of taxonomic groups based on the abundance values corresponding to the taxonomic groups constituting the pair; and
computing a correlation distance corresponding to the pair based on the correlation coefficient to obtain the interaction factor for the pair.

5. The computer implemented method as claimed in claim 1, wherein the taxa interaction profile is provided in a two dimensional layout, and wherein the taxonomic groups are provided on an axis of the two dimensional layout.

6. The computer implemented method as claimed in claim 1, wherein determining the force factor for each of the plurality of the environmental sample comprises:
determining a center of taxonomic arrangement, based on the taxa interaction profile and a cumulative total of normalized abundance values of each of the taxonomic groups in each of the environmental samples;
computing an initial position of the environmental sample in the taxa interaction profile, based on the center of taxonomic arrangement and an initial height of the environmental samples in a graphical layout; and
determining the force vector on each of the plurality of the environmental samples due to each of the taxonomic groups, based on the abundance value of the taxonomic group and the initial position of the environmental sample, wherein the force factor for the environmental sample is based on cumulative sum of corresponding force vectors.

7. The computer implemented method as claimed in claim 6, wherein computing the initial position further comprises determining the initial height based on one or more dimension parameters, the dimension parameters include total number of taxonomic groups, size of an axis on which the taxonomic groups are to be placed, and size of a display screen on which the community structure analysis profile is to be displayed.

8. The computer implemented method as claimed in claim 6, wherein clustering the plurality of the environmental samples further comprises:
determining a final position of the each of the plurality of the environmental sample in the community structure analysis profile, based on corresponding force factor; and providing, each of the environmental sample, in the taxa interaction profile at a corresponding final position to generate the community structure analysis profile.

9. A community structure analysis (CSA) system comprising:
a processor; and
a memory coupled to the processor, the memory comprising:
a sequence creation module configured to create a plurality of metagenomic sequences by sequencing genetic material obtained from each of a plurality of environmental sample, wherein the plurality of the metagenomic sequences are analyzed to identify a corresponding taxonomic group;
a taxa interaction module configured to,
determine an abundance value for each of taxonomic groups in each of a plurality of environmental samples, based on a taxonomic summary file associated with each of the plurality of environmental sample; and
compute an interaction factor for each pair of the taxonomic groups in each of the plurality of environmental samples, based in part on abundance values, wherein the interaction factor is indicative of a degree of interaction between a pair of taxonomic groups from among the taxonomic groups; and
a community structure (CS) analysis module configured to,
create a taxa interaction profile based on interaction factors, wherein the taxa interaction profile is indicative of interactions among the taxonomic groups;
compute a force vector acting on each of the plurality of the environmental samples due to each of the taxonomic groups, based on the abundance value of each of the taxonomic groups, wherein the force vector is indicative of virtual force exerted by each of the taxonomic groups on the environmental sample;
determine a force factor corresponding to each of the plurality of environmental sample, based on force vectors corresponding to the environmental sample, the force factor being representative of a combined interaction pattern of the constituent taxonomic groups on the corresponding environmental sample; and
cluster the plurality of the environmental samples based on corresponding force factors to generate a community structure analysis profile, wherein the community structure analysis profile is indicative of a comparative representation of community structures within the plurality of the environmental samples, and wherein the community structure analysis profile includes each of the plurality of environmental samples and each of the plurality of taxonomic groups as a node, and wherein an edge is assigned between an environmental sample and a taxonomic group, and
wherein, in the community structure analysis profile, the clustering places each of the plurality of environmental samples in the vicinity of one or more environmental samples having a similar community structure and in the vicinity of one or more taxonomic groups that are abundant in the environmental sample.

10. The CSA system as claimed in claim 9, wherein the CS analysis module is further configured to:
  select a taxonomic group from the taxonomic groups;
  associate a rank with each of remaining taxonomic groups based on the interaction factors corresponding to each of the remaining taxonomic groups with respect to the selected taxonomic group; and
  cluster the taxonomic groups based on ranks to create the taxa interaction profile.

11. The CSA system as claimed in claim 9, wherein the CS analysis module is further configured to:
  determine a center of taxonomic arrangement, based on the taxa interaction profile and a cumulative total of normalized abundance values of each of the taxonomic groups in each of the environmental samples;
  compute an initial position corresponding to each of the plurality of the environmental samples based on an initial height of the environmental samples in a graphical layout and the center of taxonomic arrangement;
  determine the force vector acting on each of the plurality of the environmental samples due to each of the taxonomic groups, based on the initial position of the corresponding environmental sample and the abundance value of each of the taxonomic groups, wherein the force factor for the environmental sample is based on cumulative sum of corresponding force vectors; and
  compute a final position corresponding to each of the plurality of the environmental samples based on the corresponding force factor to generate the community structure analysis profile.

12. The CSA system as claimed in claim 11, wherein the CS analysis module is configured to determine the initial height based on one or more dimension parameters, the dimension parameters include total number of taxonomic groups, size of an axis on which the taxonomic groups are to be placed, and a size of a display screen on which the community structure analysis profile is to be displayed.

13. The CSA system as claimed in claim 9, wherein the taxa interaction module is configured to:
  determine a correlation coefficient between the pair of taxonomic groups based on the abundance values corresponding to the taxonomic groups constituting the pair; and
  compute a correlation distance corresponding to the pair based on the correlation coefficient to obtain the interaction factor for the pair.

14. A non-transitory computer-readable medium having embodied thereon a computer program for executing a method for analyzing community structures within a plurality of environmental samples, the method comprising:
  creating a plurality of metagenomic sequences by sequencing genetic material obtained from each of the plurality of environmental sample, wherein the plurality of the metagenomic sequences are analyzed to identify a corresponding taxonomic group;
  determining an abundance value for each of taxonomic groups in each of a plurality of environmental samples based on a taxonomic summary file associated with a corresponding environmental sample;
  computing an interaction factor for each pair of the taxonomic groups in the plurality of environmental samples, based on abundance values, wherein the interaction factor is indicative of a degree of interaction between a pair of taxonomic groups from among the taxonomic groups;
  creating a taxa interaction profile based on interaction factors, wherein the taxa interaction profile is indicative of interactions among the taxonomic groups;
  computing a force vector acting on each of the plurality of the environmental samples due to each of the taxonomic groups, based on the abundance value of each of the taxonomic groups, wherein the force vector is indicative of virtual force exerted by each of the taxonomic groups on the environmental sample;
  determining a force factor corresponding to each of the plurality of environmental sample, based on the force vectors corresponding to the environmental sample, the force factor being representative of a combined interaction pattern of the constituent taxonomic groups on the corresponding environmental sample; and
  cluster the plurality of the environmental samples based corresponding force factors to generate a community structure analysis profile, wherein the community structure analysis profile is indicative of a comparative representation of the community structures within the plurality of environmental samples, and wherein the community structure analysis profile includes each of the plurality of environmental samples and each of the plurality of taxonomic groups as a node, and wherein an edge is assigned between an environmental sample and a taxonomic group, and
  wherein, in the community structure analysis profile, the clustering places each of the plurality of environmental samples in the vicinity of one or more environmental samples having a similar community structure and in the vicinity of one or more taxonomic groups that are abundant in the environmental sample.

15. The non-transitory computer-readable medium as claimed in claim 14, wherein the determining further comprises normalizing the abundance value for each of the taxonomic groups based on a size of the corresponding environmental sample.

16. The non-transitory computer-readable medium as claimed in claim 14, wherein computing the interaction factor for each pair of the taxonomic groups comprises:
  determining a correlation coefficient between the pair of taxonomic groups based on the abundance values corresponding to the taxonomic groups constituting the pair; and
  computing a correlation distance corresponding to the pair based on the correlation coefficient to obtain the interaction factor for the pair.

17. The non-transitory computer-readable medium as claimed in claim 14, wherein the taxa interaction profile is provided in a two dimensional layout, and wherein the taxonomic groups are provided on an axis of the two dimensional layout.

18. The non-transitory computer-readable medium as claimed in claim 14, wherein creating the taxa interaction profile comprises:
  selecting a taxonomic group from the taxonomic groups;
  associating a rank with each of remaining taxonomic groups based on the interaction factors corresponding to each of the remaining taxonomic groups with respect to the selected taxonomic group; and
  clustering the taxonomic groups based on ranks to create the taxa interaction profile.

19. The non-transitory computer-readable medium as claimed in claim 14, wherein the generating comprises;
  determining a center of taxonomic arrangement based on the taxa interaction profile and a cumulative total of normalized abundance values of each of the taxonomic groups in each of the environmental samples;
  computing an initial position corresponding to each of the plurality of the environmental samples based on an initial height of the environmental samples in a graphical layout and the center of taxonomic arrangement;

determining the force vector acting on each of the plurality of the environmental samples due to each of the taxonomic groups, based on the initial position of the corresponding environmental sample and the abundance value of each of the taxonomic groups wherein the force factor for the environmental sample is based on cumulative sum of corresponding force vectors; and computing a final position corresponding to each of the plurality of the environmental samples based on the corresponding force factor to generate the community structure analysis profile.

* * * * *